US009610063B2

(12) United States Patent
Foroughi et al.

(10) Patent No.: US 9,610,063 B2
(45) Date of Patent: Apr. 4, 2017

(54) METHODS AND APPARATUS FOR ULTRASOUND STRAIN IMAGING

(75) Inventors: Pezhman Foroughi, Baltimore, MD (US); Emad Boctor, Baltimore, MD (US); Gregory Hager, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 658 days.

(21) Appl. No.: 13/073,683

(22) Filed: Mar. 28, 2011

(65) Prior Publication Data

US 2011/0237945 A1   Sep. 29, 2011

Related U.S. Application Data

(60) Provisional application No. 61/318,040, filed on Mar. 26, 2010.

(51) Int. Cl.
| A61B 8/14 | (2006.01) |
| A61B 8/00 | (2006.01) |
| A61B 8/08 | (2006.01) |

(52) U.S. Cl.
CPC .......... *A61B 8/4245* (2013.01); *A61B 8/4254* (2013.01); *A61B 8/4263* (2013.01);
(Continued)

(58) Field of Classification Search
CPC ..... A61B 8/4245; A61B 8/485; A61B 8/5215; A61B 8/4254; A61B 8/58; A61B 8/4263
See application file for complete search history.

(56) References Cited

U.S. PATENT DOCUMENTS

| 5,107,837 A | 4/1992 | Ophir et al. |
| 5,474,070 A | 12/1995 | Ophir et al. |
(Continued)

FOREIGN PATENT DOCUMENTS

WO   2010/081094 A2   7/2010

OTHER PUBLICATIONS

Foroughi et al., "Application of External Tracking in Ultrasound Elasticity Imaging". Proceedings of SPIE vol. 7629, 76291B Medical Imaging 2010: Ultrasonic Imaging, Tomography, and Therapy (presented Feb. 13, 2010, San Diego, CA; published Mar. 12, 2010).*

(Continued)

*Primary Examiner* — Long V Le
*Assistant Examiner* — Colin T Sakamoto
(74) *Attorney, Agent, or Firm* — Venable LLP; Henry J. Daley; Laura G. Remus

(57) ABSTRACT

A system and method for improved ultrasound strain imaging includes using data from a tracking system to enhance the quality of ultrasound strain image and to reduce the dependency of image quality of the user's expertise. The tracking information is synchronized with the RF frames and interpolated to find the transformation corresponding to each frame. The RF frames with their transformations are incorporated into calculation of ultrasound strain images. The tracking system may be an optical tracker, electromagnetic tracker, accelerometer, or a structured light system. The structured light system may also be used for probe calibration, by calibrating the surface of the probe pre-operatively. In addition, a relative Young's Modulus may be calculated using tracking information that is independent from the distribution of input force.

12 Claims, 7 Drawing Sheets

(52) U.S. Cl.
CPC ............ *A61B 8/485* (2013.01); *A61B 8/5215* (2013.01); *A61B 8/58* (2013.01)

(56) References Cited

U.S. PATENT DOCUMENTS

| | | | |
|---|---|---|---|
| 6,270,459 | B1 | 8/2001 | Konofagou et al. |
| 6,508,768 | B1 | 1/2003 | Hall et al. |
| 6,687,625 | B2 | 2/2004 | Srinivasan et al. |
| 6,726,629 | B1 | 4/2004 | Frinking et al. |
| 7,103,212 | B2 | 9/2006 | Hager et al. |
| 7,457,450 | B2 | 11/2008 | Bruder et al. |
| 7,515,680 | B2 | 4/2009 | Schaller et al. |
| 7,867,167 | B2 | 1/2011 | Boctor et al. |
| 7,901,357 | B2 | 3/2011 | Boctor et al. |
| 2004/0254620 | A1 | 12/2004 | Lacoste et al. |
| 2005/0261591 | A1* | 11/2005 | Boctor et al. ............ 600/462 |
| 2005/0267368 | A1 | 12/2005 | Boctor et al. |
| 2006/0052696 | A1 | 3/2006 | Shiina et al. |
| 2008/0196506 | A1 | 8/2008 | Satoh et al. |

OTHER PUBLICATIONS

Foroughi et al., "Multi-modality Fusion of CT, 3D Ultrasound, and Tracked Strain Images for Breast Irradiation Planning". Proceedings of SPIE vol. 7265, 72651 B Medical Imaging 2009: Ultrasonic Imaging and Signal Processing (presented Feb. 7, 2009, Lake Buena Vista, FL; published Mar. 13, 2009).*
Ophir et al., "Elastorgraphy: ultrasonic imaging of tissue strain and elastic modulus in vivo". European journal of ultrasound 3.1 (1996): 49-70.*
Krouskop et al., "Elastic moduli of breast and prostate tissues under compression". Ultrasonic imaging 20.4 (1998): 260-274.*
Ophir, J. et al., "Elastography: ultrasonic estimation and imaging of the elastic properties of tissues", Annu. Rev. Biomed. Eng., 213, 203-233 (1999).
Garra, B. et al., "Elastography of breast lesions: initial clinical results", Radiology 202, 79-86 (1997).
Lindop, J.E. et al., "An intelligent interface for freehand strain imaging", Ultrasound Med. Biol. Nov. 7, 2008, pp. 1117-1128, vol. 34, No. 7.
Jiang, J. et al., "A novel strain formation algorithm for ultrasonic strain imaging", IEEE Ultrasonics Symposium, 1282-1285 (2006).
Foroughi, P. et al., "Robust elasticity imaging using external tracker", IEEE Int. Symp. Biomed. Imag. (2009) pp. 209-212.
Wagner, R. et al., "Statistics of speckle in ultrasound B-Scans", IEEE Trans. Sonics and Ultrasonics, May 1983, pp. 251-268, vol. 30, No. 3.
Shankar, P., "A general statistical model for ultrasonic backscattering from tissues", IEEE Trans. Ultrason. Ferroelectr. Freq. Control, May 2000, pp. 727-736, vol. 47, No. 3.
Prager, R. et al., "Sensorless freehand 3-d ultrasound using regression of the echo intensity", Ultrasound Med. Biol., (2003) pp. 437-446, vol. 29, No. 3.
Varghese, T. et al., "A theoretical framework for performance characterization of elastography: the strain filter", IEEE Transactions on Ultrasonics, Ferroelectrics and Frequency Control, Jan. 1997, pp. 164-172, vol. 44, No. 1.
Cespedes, I. et al., "Methods for estimation of subsample time delays of digitized echo signals", Ultrasound Imaging, (1995) pp. 142-171, vo. 17, No. 2.
Varghese, T. et al., "Performance optimization in elastography: multicompression with temporal stretching", Ultrasonic Imaging, (1996), pp. 193-214, vol. 8.
Chandra, A. et al., "Experience of ultrasound-base daily prostate localization", Int. J. Radiation Oncology Biol. Phys., Dec. 12, 2002, pp. 436-447, vol. 56 No. 2.
Itoh, A. et al., "Breast disease: clinical application of US elastography for diagnosis", Radiology, May 2006, pp. 341-350, vol. 239, No. 2.
Jaffray, D. et al., "Flat-panel cone-beam computed tomography for image-guided radiation therapy", Int. J. Radiation Oncology Biol. Phys., Apr. 3, 2002, pp. 1337-1349, vol. 53, No. 5.
Letourneau, D. et al., "Cone-beam-CT guided radiation therapy: technical implementation", Radiotherapy and Oncology, May 10, 2005, pp. 279-286, vol. 75.
Landis, D. et al., "Variability among breast radiation oncologists in delineation of the postsurgical lumpectomy cavity", Int. J. Radiation Oncology Biol. Phys., Nov. 14, 2007, pp. 1299-1308, vol. 67, No. 5.
Rivaz, H. et al., "Ultrasound elastography: a dynamic programming approach", IEEE Transactions on Medical Imaging, Oct. 2008, pp. 1373-1377, vol. 27, No. 10.
Fitzpatrick, J., et al., "The distribution of target registration error in rigid-body point-based registration", IEEE Transactions on Medical Imaging, Sep. 2001, pp. 917-927, vol. 20, No. 9.
Ophir, J., et al., "Elastography: A quantitative method for imaging the elasticity of biological tissues", Ultrasonic Imaging, (1991), pp. 111-134, vol. 13.
Baglan, K., et al., "Accelerated partial breast irradiation using 3D conformal radiation therapy (3D-CRT)", Int. J. Radiation Oncology Biol. Phys., Jul. 31, 2001, pp. 302-311, vol. 55, No. 2.
Langen, K., et al., "Evaluation of ultrasound-based prostate localization for image-guided radiotherapy", Int. J. Radiation Oncology Biol. Phys., May16, 2003, pp. 635-644, vol. 57, No. 3.
Nikolaou, K., et al., "Flat panel computed tomography of human ex vivo heart and bone specimens: initial experience", Eur Radiol, Nov. 20, 2004, pp. 329-333, vol. 15.
Vences, L., et al., "Target motion measurement without implanted markers and its validation by comparison with manually obtained data", Med. Phys., Oct. 24, 2005, pp. 3431-3439, vol. 32, No. 11.
Miyanaga, N., et al., "Tissue elasticity imaging for diagnosis of prostate cancer: a preliminary report", International Journal of Urology, Jun. 14, 2006, pp. 1514-1518, vol. 13.
Chaturvedi, P., et al., "Testing the limitations of 2-D companding for strain imaging using phantoms", IEEE Transactions on Ultrasonics, Ferroelectrics, and Frequency Control, Jul. 1998, pp. 1022-1031, vol. 45, No. 4.
Benda, R., et al., "Breast boost: are we missing the target?", Cancer, Feb. 15, 2003, pp. 905-909, vol. 97, No. 4.
Zhang, H., et al., "Freehand 3D ultrasound calibration using an electromagnetically tracked needle", SPIE Conference Proceedings vol. 6141; Medical Imaging Mar. 13, 2006.
Emelianov, S., et al., "Triplex ultrasound: elasticity imaging to age deep venous thrombosis", Ultrasound in Med. & Biol., Mar. 13, 2002, pp. 757-767, vol. 28, No. 6.
Jiang, F. et.al., "A novel image formation method for ultrasonic strain imaging", Ultrasound Med Biol., Apr. 2007, pp. 643-652, vol. 33, No. 4.
Shoemake, K., "Animating rotation with quaternioncurves", Proc. of SIGGRAPH, (1985), pp. 245-254.

* cited by examiner

METHODS AND APPARATUS FOR ULTRASOUND STRAIN IMAGING

REFERENCE TO RELATED APPLICATIONS

This application claims the benefit of U.S. Provisional Patent Application No. 61/318,040, filed on Mar. 26, 2010, which is hereby incorporated by reference for all purposes as if fully set forth herein.

FIELD OF THE INVENTION

The present invention pertains to a method and system for ultrasound strain imaging. More particularly, the present invention pertains to a method and system for ultrasound strain imaging using an external tracker.

BACKGROUND OF THE INVENTION

Ultrasound imaging has become a widely used medical imaging modality, due in part to its effectiveness in safely imaging tissue, its ease of use, and lower cost. Ultrasound has become an essential imaging tool in applications such as identifying tissue anomalies, monitoring fetal development, and assisting in guiding surgical devices in invasive treatments.

More recently, strain imaging has been shown helpful in numerous medical applications, especially in the detection and diagnosis of cancer. In addition, strain imaging may be used for monitoring ablation and deep vein thrombosis. However, generating reliable, high-quality ultrasound strain images from freehand palpations is a challenging task. Strain imaging is highly sensitive to the proper hand motion and the skill of the user.

For example, the best results are achieved when the user compresses and decompresses the tissue uniformly in the axial direction with the proper hand motion. However, it is difficult to control the compression rate as it is governed by hand motion and the frame rate of RF data. Also, small lateral or out-of-plane motions can compromise the quality of images. However, it is difficult to induce pure axial motion with freehand compression.

Sophisticated algorithms have developed to address this problem. However, these algorithms only partially address the problem by compensating for in-plane motions and applying smoothness constraints. The images are also hard to interpret, and artifacts—caused by failure of the strain estimation algorithm or poor hand motion—may be mistaken for lesions inside the soft tissue. As such, there is a need in the art for a strain imaging technique that is not affected by poor hand motion and other sources of signal decorrelation.

To improve the reliability, quality metrics such as persistence in strain images have been developed, as discussed, for example, by JIANG, F. et. al., in their article "*A novel image formation method for ultrasonic strain imaging*", Ultrasound Med Biol., April 2007, pp. 643-652, Vol. 33, No. 4, the entire disclosure of which is incorporated by reference herein. This quality indicator is calculated for each image and provided to the user as feedback. Persistence is also used to merge multiple strain images together. To measure the persistence, strain is computed for two pairs of echo frames, and the resulting images are correlated.

Although these techniques offer a major advantage, there remain several limitations. First, the strain has to be estimated before the calculation of the quality metric. With typical ultrasound settings, the frame rate can reach more than 30 Hz. For subsequent frames, an efficient implementation of this image-based metric might cope with this rate. Nonetheless, it is difficult and time consuming to try all combinations in a series of frames. Moreover, the quality metric will not be able to provide feedback to the user regarding whether he/she should adjust the palpation in a certain direction. Also, there is minimal control over the strain.

Accordingly, there is a need in the art for a system and method of improved strain imaging, which does not rely upon complicated algorithms or the experience of the user.

SUMMARY

According to a first aspect of the present invention, a method for providing ultrasonic strain imaging comprises placing an ultrasound probe onto a target area to be imaged, applying palpations to the target area, acquiring a sequence of RF frames during palpations of the target area, measuring positions and orientations of the ultrasound probe at each the RF frame in the sequence of the RF frames, synchronizing each of the positions and orientations of the ultrasound probe to a respective RF frame in the sequence of RF frames, automatically selecting multiple pairs of RF frames from an approximately same location and orientation from the synchronized sequence of RF frames by minimizing a cost function, the cost function evaluating the relative motion of any two image frames based upon the measured positions and orientations of the two image frames, further selecting, from the automatically selected multiple pairs of RF frames, multiple pairs of RF frames with a desired strain, calculating strain values for each of the selected multiple pairs of RF frames with the desired strain, aligning and fusing images of the selected multiple pairs of RF frames with the desired strain from the approximately same location and orientation to generate a final strain image, and displaying the final strain image.

According to a second aspect of the present invention, a system for providing ultrasonic strain imaging comprises an ultrasound probe for acquiring a sequence of RF frames during palpations of a target area, an external tracking device for measuring positions and orientations of the ultrasound probe at each the RF frame in the sequence of RF frames, a processor having a computer readable medium encoded with a program for optimizing the ultrasonic strain imaging, the program for synchronizing each of the positions and orientations of the ultrasound probe to a respective RF frame in the sequence of RF frames, automatically selecting multiple pairs of RF frames by minimizing a cost function which evaluates relative motion of any two image frames based upon the measured positions and orientations, calculating strain values for each of the selected multiple pairs of RF frames with the desired strain, and aligning and fusing images of the selected multiple pairs of RF frames with the desired strain from the approximately same location and orientation to generate a final strain image, and a display for displaying the final strain image.

According to a third aspect of the present invention, computer-readable medium comprising software, wherein, when executed by a computer, causes the computer to receive a sequence of RF frames during palpations of a target area, receive positions and orientations of the ultrasound probe at each said RF frame in said sequence of said RF frames, synchronize each of the positions and orientations of the ultrasound probe to a respective RF frame in the sequence of RF frames, select multiple pairs of RF frames from an approximately same location and orientation from said synchronized sequence of RF frames by minimizing a cost function, said cost function evaluating the relative motion of any two image frames based upon the measured positions and orientations of said two image frames, select, from the automatically selected multiple pairs of RF frames, multiple pairs of RF frames with a desired strain, calculate strain values for each of said selected multiple pairs of RF frames with the desired strain, and align and fuse images of the selected multiple pairs of RF frames with the desired strain from the approximately same location and orientation to generate a final strain image.

According to a fourth aspect of the present invention, a method of strain imaging comprises projecting a structured light pattern onto a surface of a target area to be imaged, acquiring a first set of images of the structured light pattern on the surface of the target area, said first set of images for reconstructing the surface of the target area, placing an ultrasound probe onto the target area, acquiring a second set of images including the surface of the target area and the ultrasound probe to determine the location of the probe, applying palpations to the target area, acquiring strain image data of the target area, constructing a finite element model based upon the first set of images, second set of images, and strain image data, and using the finite element model to solve for Young's Modulus to generate a strain image.

According to a fifth aspect, a method for performing intraoperative calibration of an ultrasonic probe comprises projecting a structured light pattern onto a surface of the ultrasonic probe to generate a surface model of said ultrasonic probe, the ultrasonic probe for generating an ultrasound image, calibrating the surface model of the ultrasonic probe to the ultrasound image pre-operatively, attaching a sensor to the surface of the ultrasonic probe at a sensor location, determining a transformation between the surface model of the ultrasonic probe and the sensor at the sensor location, and computing a probe calibration matrix based upon the pre-operative calibration of the surface model of the ultrasonic probe to the ultrasound image and the transformation between the surface model of the probe and the sensor.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a system and method for strain imaging using information from an external tracker. As is known in the art, an ultrasound probe is often tracked in navigation/guidance systems to provide spatial information to form freehand 3D ultrasound, or to facilitate multi-modality registration. According to features of the present invention, the tracking data is exploited to enhance the quality of the strain images. It should be understood that strain imaging includes, but is not limited to, elastography and thermal imaging. A more detailed description of thermal imaging is described in U.S. patent application Ser. No. 12/712,019, the entire disclosure of which is incorporated by reference herein.

Figure 1:
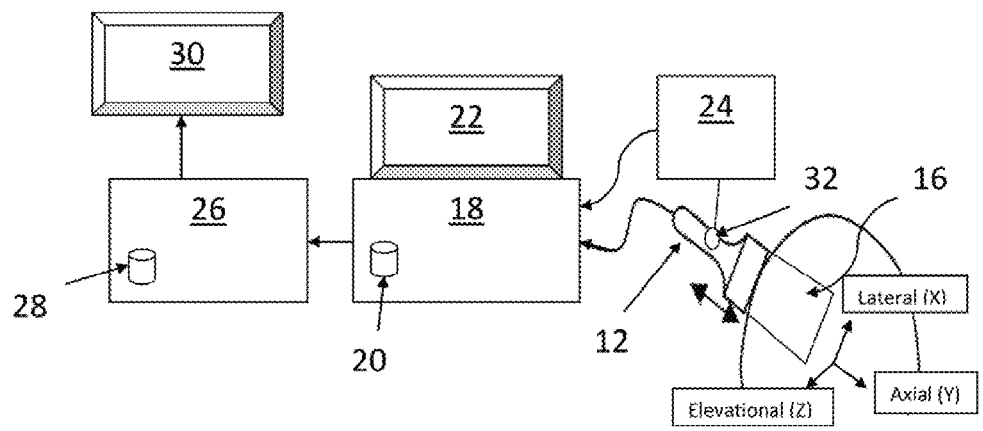
FIG. 1 is a schematic of an exemplary system and method according to the features of the present invention.

According to FIG. 1, a basic schematic of an ultrasonic imaging system 10 that may be used in accordance with the present invention is illustrated. The ultrasonic imaging system 10 includes an ultrasonic probe 12 for imaging the target area 14 of a patient. According to known principles, the ultrasonic probe 12 transits and receives energy in a scan plane 16, which may be acquired by an ultrasonic processor 18 (with a memory device 20), and displayed on a user interface 22. The memory device 20 may include one or more computer readable storage media, as well as a program having machine readable instructions for performing processing necessary to form B-mode images.

All of the components of ultrasonic imaging system 10 may be parts of an existing commercial ultrasound system, with memory device 20 having additional machine readable instructions for performing the processes disclosed herein. Alternatively, a separate processor 26 with a memory device 28 may be used. Like the memory device 20, the memory device 28 would include a program having machine readable instructions for performing the necessary algorithms to determine the optimal frames to use for strain imaging, as will be described in more detail below. Once the strain imaging is processed, it may be displayed on interface 30. One skilled in the art will readily appreciate that many variations to ultrasonic system 10 are possible and within the scope of the invention. For example, the ultrasonic system 10 may be a 2-dimensional or 3-dimensional system, but other systems are possible depending on application and design preference.

According to known principles, strain imaging is generated by palpating the ultrasonic probe 12 in the axial "Y" direction. As is known in the art, the ultrasonic probe 12 is placed onto the target area 14 to be imaged. Palpations are applied to the target area 14, wherein a sequence of RF frames is acquired by the processor 18 (or processor 26) during palpations. According to the prior art, consecutive frames of RF data are used to generate the strain image. However, using tracking information, the present invention allows for optimal image frames to be determined and used for more precise strain imaging.

With continued reference to FIG. 1, according to an exemplary embodiment, a tracking system 24 is used to monitor the position and orientation of the ultrasound probe 12. The tracking information is used in connection with the RF data acquired by the probe 12 to determine optimum frames to use for higher quality strain images, even when the palpations are poor. Accordingly, the tracking information may be sent to memory device 20, which includes machine readable instructions for performing the necessary algorithms to determine the optimal frames to use for strain imaging. However, the tracking information may also be sent to the separate processor 26, and stored in memory device 28, as described above.

In accordance with features of the present invention, the tracking system 24 may be an optical tracker, an electromagnetic tracker, an accelerometer-gyroscope, or the like. In this regard, the ultrasonic probe 12 may include at least one sensor 32 which is monitored by the tracking system 24. Examples of sensors include but are not limited to electromagnetic tracking sensors, optical sensors, accelerometers-gyroscopes, or the like. In addition, an ablation needle may be used for tracking. Likewise, a robotic arm may be used for tracking when the probe is held by a medical robot.

Figure 2:
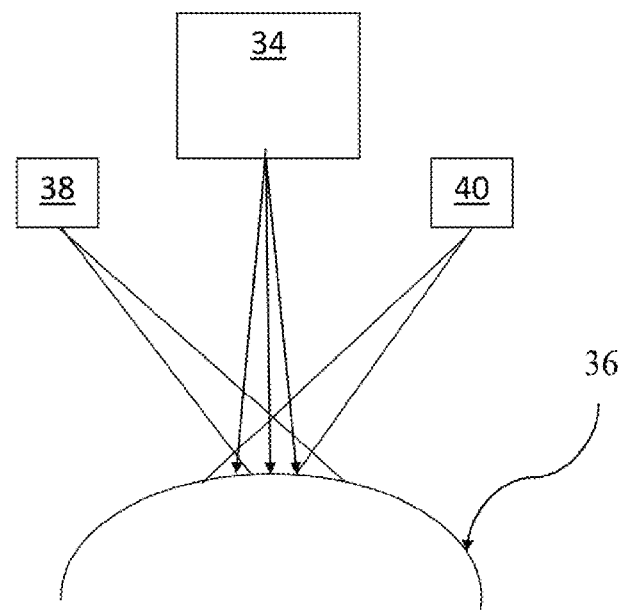
FIG. 2 is a schematic of an exemplary structured light system used in connection with the system and method of the present invention.

Alternatively, the surface of the ultrasonic probe 12 or target area 14 may be tracked, as is known in the art. For example, a structured light system may be used to project light onto the surface of the probe and/or target area, which tracks the probe and/or target area by its shape. With reference to FIG. 2, a projector 34 projects patterned light onto a surface 36. The patterned light is viewed by two cameras 38 and 40 which are spaced apart, preferably stereo cameras. The data collected from the two cameras 38 and 40 is used to construct a 3-dimensional image of the surface, as well as to determine how much a surface has been compressed. An example of a structured light system can be found in U.S. Pat. No. 7,103,212, the entire content of which is incorporated by reference herein.

In addition, an internal surface of a patient may also be used as the tracking information. For example, during liver surgery, a structured light system can be used to determine how much the liver has been compressed or palpated to produce strain images. A tracking system that is used to track the surface of a patient is described in WO 2010/081094, the entire content of which is incorporated by reference herein.

Figure 3:
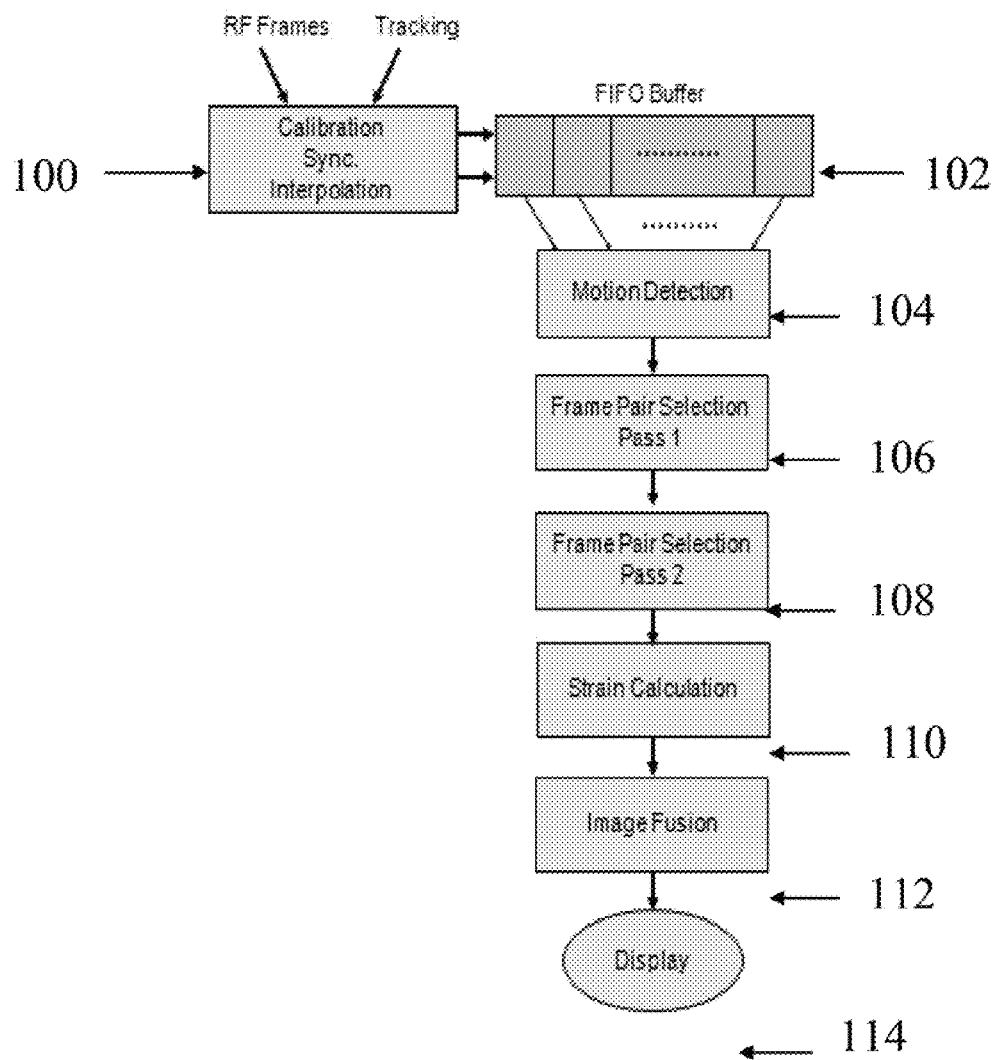
FIG. 3 is a basic flowchart of an exemplary process for generating an ultrasound strain image according to features of the present invention.

With reference to FIG. 3, a basic flowchart of an exemplary process for generating an ultrasound strain image according to features of the present invention is shown, which may be implemented by software. As described above, the software may be stored and run on the ultrasonic processor 18 (FIG. 1), or the separate processor 26 (FIG. 1). As shown in FIG. 1, the tracking information and RF frames are sent to a processor, where the data is manipulated to form optimal strain imaging according to features of the present invention.

At step 100 (FIG. 3), the tracking information and sequence of RF frames are processed so that each of the positions and orientations of the ultrasound probe are calibrated to and synchronized with a respective RF frame in the sequence of RF frame. In this way, the same axial palpation for strain imaging can be used for synchronization. In particular, when synchronizing the data, the constant delay between RF and tracking information may be estimated as the data is collected. In addition, small jitters in delay may be compensated.

For example, assuming uniform stiffness of the soft tissue, the global axial compression is recovered from the image by correlating the first frame and the stretched version of the next frame. The compression values are integrated over a period of time to get the compression with respect to the first frame in that period. This value is then normalized and matched with the normalized axial motion from the external tracker. Normalization is important since the magnitude of global axial motion in the strain image varies depending on the overall stiffness of the soft tissue.

Figure 4:
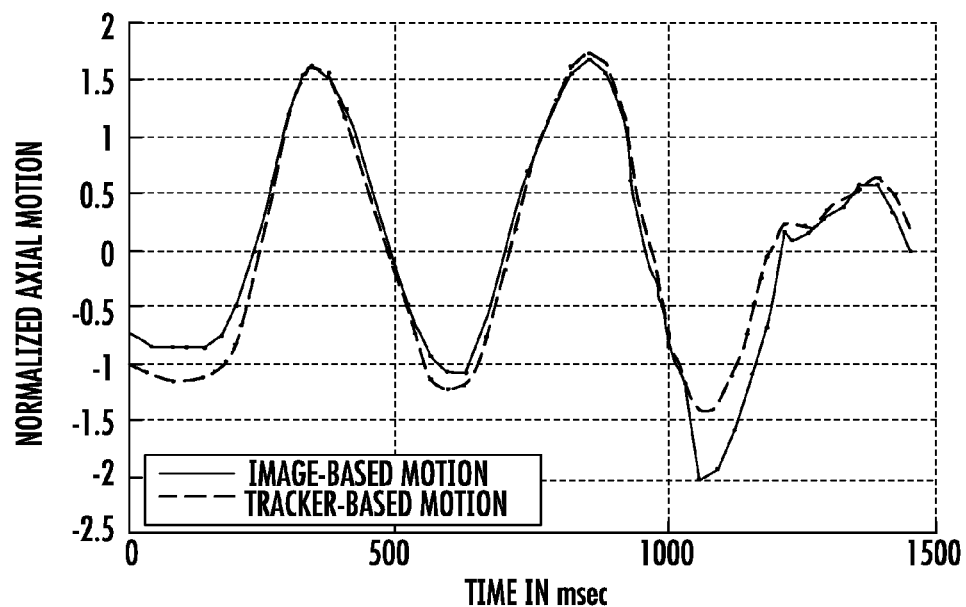
FIG. 4 is a graphical representation of the normalized axial motion of the image-based motion and the tracker-based motion.

For normalization, the mean of the signal over the synchronization period is subtracted from the signal, and the result is divided by the standard deviation. The last step is to interpolate the tracking data to find the transformation for RF frames. The translations and rotations may be separately interpolated using "spline" interpolation for the translations and "spherical linear interpolation" (Slerp) for the rotations, as described by K. Shoemake in "*Animating rotation with quaternioncurves,*" Computer Graphics (Proc. of SIGGRAPH), pp. 245-254 (1985), the entire disclosure of which is incorporated by reference herein. FIG. 4 shows an example of two signals after synchronization. However, other methods of calibration and synchronization are possible, and within the scope of the present invention.

With reference back to FIG. 3, the RF frames along with their corresponding transformation are preferably stored in a first-in, first out (FIFO) buffer 102. The buffer 102 provides a location in which the pools of RF frames may be stored. Preferably, the size of the buffer is large enough to include roughly a half cycle of freehand palpation, but may be larger or smaller, according to application and design preference.

At step 104 (Motion Detection), all RF frames that are taken from approximately the same cross section are found. At step 106, a first "Frame Pair Selection Pass 1" is performed. Relying on the tracking information, frames with improper motion are rejected. The resulting data is then filtered through the "Frame Pair Selection Pass 2", at step 108. In this step, image content of the RF frame is used to determine the multiple frame pairs with a desired strain. At step 110, the "Strain Calculation" compensates for global motion and calculates the strain for the selected pairs. In the "Image Fusion" step 112, the strain images are fused and aligned, and final normalization is applied. At step 114, the final strain image is displayed on a display.

Further details of the algorithms associated with the present invention will be described in more detail below. As discussed above, the algorithms are implemented by a software program. In generating the algorithm for performing the strain imaging, the task is to find appropriate RF pairs that can generate high-quality strain images. In the past, only consecutive frames were used for strain imaging. The present invention provides a methodology for selecting the optimum set of RF pairs, which may not necessarily be consecutive frames. Accordingly, a cost function is derived to determine which optimum pairs may be used to generate the best strain image. The cost function evaluates the relative motion of any two image frames based upon the measured positions and orientations of the two image frames.

To start, a distance function is defined between two frames of RF data. For this purpose, a model of image decorrelation may be used in presence of out-of plane and lateral motion. RF signal is often modeled as the collective response of scatterers randomly distributed within the resolution cell of the ultrasound. Each scatterer is assumed to have an amplitude governed by the shape of the resolution cell and a phase which is distributed from 0 to π uniformly at random. Considering a Gaussian shape for the resolution cell, the correlation may be calculated as a function of out-Of-plane motion to be $$\exp\left(-\frac{\delta^2}{2\sigma^2}\right)$$

wherein δ and σ denote the displacement and the width of the resolution cell respectively. Although this function is only valid for fully developed speckle, it provides a convenient estimate of correlation.

Extending this formula to both out-of-plane and lateral displacements, the energy function, E(x, z), is defined as follows:

$$E(D_x, D_z) = \exp(-K_x \cdot D_x^2 - K_z \cdot D_z^2), \quad (1)$$

where $D_x$ and $D_z$ represent the displacement in out-of-plane and lateral directions. E does not depend on axial motion ($D_y$) since displacement in the axial direction is necessary for strain estimation. $K_x$ and $K_z$ determine the sensitivity to a certain direction. In order to be able to use this function, component-wise metric representing the distance of two frames is needed given their homogeneous transformations. The relative transformation is computed between them. Suppose $a=[a_x\ a_y\ a_z]^T$ is the axis-angle representation of the relative rotation, and $t=[t_x\ t_y\ t_z]^T$ is the relative translation. Assuming a small rotation, the relative displacement of a point, $P=[x\ y\ 0]^T$, will be $d=a \times P+t$. The distance vector of two frames is then defined, $D=[D_x\ D_y\ D_z]^T$, as the RMS of the components of d for all the points in the region of interest (ROI):

$$D_x = sqrt\left\{\frac{1}{(y_2-y_1)}\int_{y_1}^{y_2}(-a_z \cdot y + t_x)^2\,dy\right\}, \quad (2)$$

$$D_y = sqrt\left\{\frac{1}{(x_2-x_1)}\int_{x_1}^{x_2}(a_z \cdot x + t_y)^2\,dx\right\},$$

$$D_z = sqrt\left\{\frac{1}{(y_2-y_1)(x_2-x_1)}\int_{x_1}^{x_2}\int_{y_1}^{y_2}(a_x \cdot y - a_y \cdot x + t_z)^2\,dy\,dx\right\},$$

where sqrt {.} returns the root. Here, ROI is assumed to be rectangular and determined by $x_1$, $y_1$, and $y_2$. The vector D provides a measure of distance for each direction separately. This vector is used in Equation (1) which gives us an estimate of "pseudo-correlation" over the ROI.

As discussed above, images are selected from a pool of RF frames that are collected from approximately the same cross-section of tissue with minimal lateral and out-of-plane motion. This may be accomplished by computing the energy function of each frame with respect to all other frames in the sequence. Then, the total energy is found for each frame as the sum of the energies of the M closest frames, where closeness implies higher energy, and M is the maximum number of frames to be selected. Then, the frame with the highest total energy (the center frame) is identified, and the M closest frames to the center frame including itself are selected. Additionally, the frames that have E of less than 0.5 with respect to the center frame are disqualified. This is applied to ensure lower number of frames are chosen when M frames from one cross-section are not available.

In the next stage, the program evaluates all possible combination of frame M pairs for strain imaging. For M frames, there are (M/2)=M(M−1)/2 pair combinations, which are compared using a slightly modified version of E. Since the pairs are directly compared, the exponent of Equation (1) is minimized in order to maximize E. A term for axial motion may be added that penalizes compressions that are higher than an optimum compression value, $t_{opt}$. Hence, a "cost function", $C_1$, is defined as follows:

$$C1(D) = K_x \cdot D_x^2 + K_y \cdot \overline{D}_y^2 + K_z \cdot D_z^2, \quad \overline{D}_y = \begin{cases} D_y - t_{opt}; & |D_y - t_{opt}| > 0 \\ 0, & |D_y - t_{opt}| \le 0 \end{cases} \quad (3)$$

where $t_{opt}$ implies the optimal strain.

Here, $t_{opt}$ is set depending on the robustness of the strain image estimation algorithm. Its value might be within the range of the resolution of the tracker. Therefore, at this stage, a penalty is not assigned for the compressions less than $t_{opt}$. If the compression is close to zero, the contrast of the reconstructed image degrades. The program may filter the pairs with low compression in the next stage using image content. Similar to the first part, a maximum number of frames with lowest cost are selected provided that the cost is lower than a threshold. The threshold is not strict to ensure acceptable pairs are not filtered.

The final pairs are selected by recovering the global lateral motion and compression by matching the two RF frames in each pair. The tracking information is used to initialize the search. For instance, the search range for compression is set to be from zero to the tracker reading in axial direction padded in both sides with the maximum error of the tracker. Given two frames $I_1$ and $I_2$, the amount of lateral motion a, and compression, b, is found by solving cross-correlation:

$$\operatorname*{argmax}_{a,b}\left\{\sum_{x,y \in C} I_1(x, y) \cdot I_2(x+a, by) + I_1(x-a, -by) \cdot I_2(x, y)\right\}. \quad (4)$$

The RF data may be normalized with standard variation and assumed to have zero mean. The speed of search may be increased by employing two steps. First, the entire image is not matched to solve for these parameters. Instead, only pixels on a grid, G, are used as described by Equation (4). The two terms of Equation (4) ensures that the search remains reciprocal, which means switching the images only affects the sign of a and b. Second, a is recovered by matching only the top part of the two images while b is fixed to one. The reason is that the displacement due to compression is minimal in that region.

Having the global motions, the cost function is modified to penalize very low compressions:

$$C2(\hat{D}) = K_x \cdot \hat{D}_x^2 + K_y \cdot \frac{|\hat{D}_x - t_{opt}|^3}{\hat{D}_y + c} + K_z \cdot D_z^2, \quad (5)$$

where $D_x$ and $D_y$ are the global motions from Equation (4) converted to mm. c is a small number that limits the cost of zero compression. Finally, the pairs with the lowest cost are selected until a maximum number of frame pairs are reached or the minimum cost grows higher than the average cost.

The last step involves computing the strain for all the selected frame pairs. In the preferred embodiment, normalized cross-correlation (NCC) is implemented to recover the displacements and least squares estimation (LSE) to calculate the strain. However, other types of correlation techniques are possible, such as Sum of Squared Difference (SSD), Sum of Absolute Difference (SAD), and Mutual Information. Before calculating strain, the global lateral motion and compression from the previous step may be compensated in one image using cubic interpolation. This is known to reduce the error of strain estimation. The final strain image. $S_{final}$ is the weighted average of all the strains:

$$S_{final} = \frac{\sum_{i=1}^{m} w_i \cdot S_i}{\sum_{i=1}^{m} w_i}, w_i = \begin{cases} \frac{\rho_i}{1-\rho_i}, & \rho_i > 0.7 \\ 0, & \text{otherwise} \end{cases} \quad (6)$$

where $\rho_i$ is the correlation coefficient for the $i^{th}$ pair after applying the displacements, and m is the number of pairs. Fusing the strains in this fashion is acceptable since the algorithm preferably only allows for compressions that are close to a predetermined amount optimal for strain estimation. Accordingly, the final strain image is displayed on the interface.

While specific equations are set forth above for deriving a particular cost function, it should be understood that other algorithms are possible and within the scope of the invention, so long as the algorithm minimizes a cost function that evaluates the relative motion of any two image frames based upon the measured positions and orientations of the two image frames.

The method and system of the present invention may be incorporated and utilized with various types of ultrasound systems, including those with motorized hardware, such as a linear actuator. According to features of the present invention, the tracking data and the measured response of the hardware may be incorporated into the estimation of the strain image.

Figure 8:
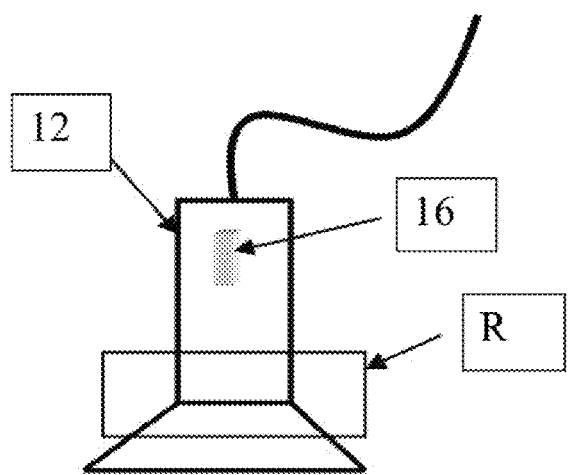
FIG. 8 is a schematic of use of the system and method of the present invention in connection with a medical robot.

With reference to FIG. 8, an ultrasonic probe 12 having a sensor 32 is connected to a robotic control R. The robotic control R automatically adjusts the palpation based on the tracking information. An example of motorized hardware for performing palpations during robotic surgery is described in U.S. Pat. No. 7,901,357, the entire contents of which of incorporated by reference herein. While U.S. Pat. No. 7,901,357 discloses a linear actuator used in connection a robotic control, motorized hardware may also be incorporated onto a probe which is held by the user. The tracking data may be used to automatically determine how the motor should move up and down. The hardware provides the suitable palpation as the user holds the ultrasound transducer over a region of interest. The hardware acts as an interface between the user and the ultrasound transducer.

Preferably, the transducer includes visual hand motion feedback to the user. The feedback provides a correctional tool for a faster learning curve for freehand strain imaging. The feedback may be in the form of a visual display, LED light, sound, or the like.

In addition, the present invention may be applied to frame motion compensation for 3D strain imaging for motorized wobbler or 2D array probes. Based on the motion of the probe during palpation, the relative displacement of the individual 2D frames from 3D RF data is corrected to avoid deformation of the 3D strain volume.

Figure 9:
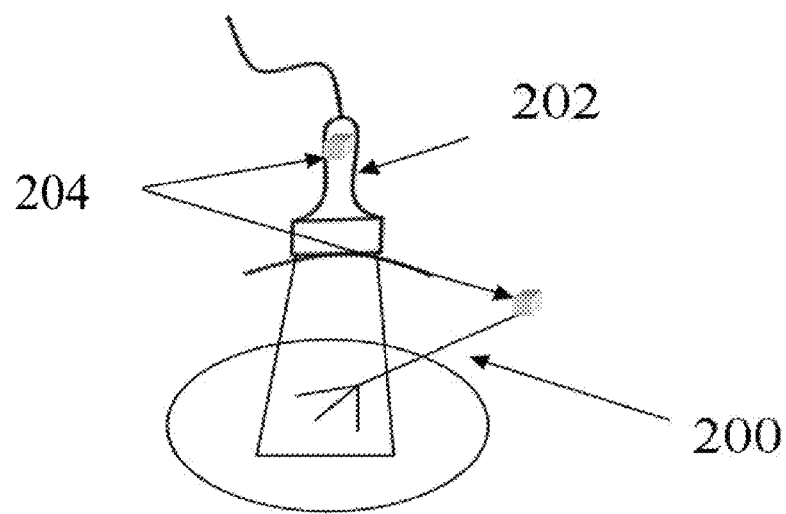
FIG. 9 is a schematic of use of the system and method of the present invention in connection with ablation treatments.

The present invention may also be used during ablation treatments. For example, as shown in FIG. 9, an ablation needle 200 is directed into tissue. In this way, the ablation needle may apply palpations towards the organ, while transducer 202 acquires acoustic images during the palpations. Preferably, both the ablation needle 200 and transducer 202 include sensors 204 for tracking of the needle 200 and transducer 202. The tracking information is used to determine the relative position of the needle 200 to the image. This information may then be directed to the strain algorithm.

Figure 10:
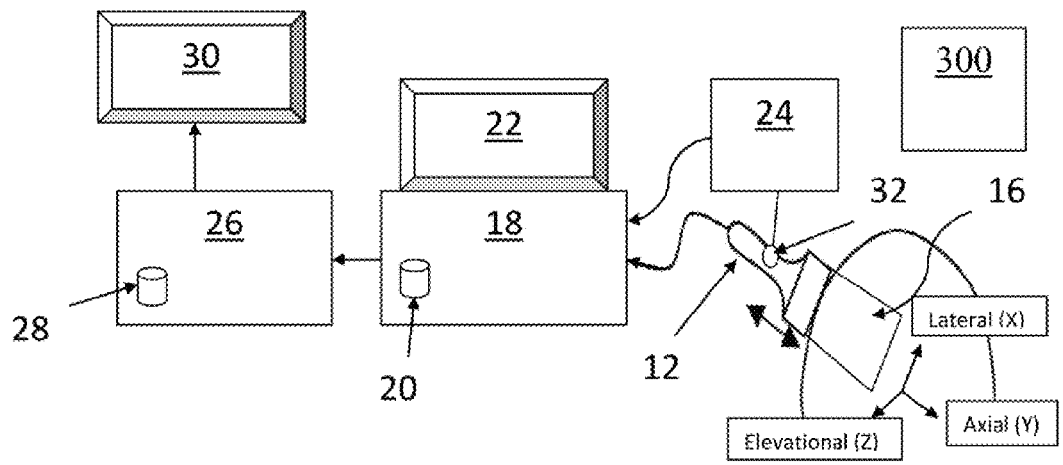
FIG. 10 is a schematic of an exemplary system and method of the present invention for fusion of the tracked strain images with CT and 3D imaging.

The present invention may also be used in connection with other imaging modalities to improve overall imaging. For example, with reference to FIG. 10, a system and method of the present invention is identical to FIG. 1, except that a CT scanner 300 is incorporated into the system. The data from the CT scanner preferably is collected in the same processor as the processor that collects the tracking information and RF data. According to features of the present invention, fiducials may be used to locally align the CT and ultrasound data.

After the CT scan is performed, the sonographer may sweep the ultrasound transducer over the lumpectomy bed. Next, the sonographer obtains individual tracked strain images from the areas of interest by gently moving the ultrasound transducer up and down. In accordance with features of the present invention, RF data is synchronized with the tracking information, and the best RF frames are used to facilitate a better strain image. While CT scanning has been particularly described above, it should be understood that the present invention may be applied to other imaging modalities, such as MRI. Features of the present invention may also be applied during photoacoustic imaging, as described in PCT/US11/24917, the entire disclosure of which is incorporated by reference herein. In particular, the transducer probe and laser source may both be tracked to help enhance the photoacoustic image formation. For example, if the laser flux is small compared to the ultrasound image, then by tracking the laser source, one can give high weight to the signal received from the small tracked flux, hence increase the final photoacoustic image quality. Another example, by tracking the laser source, one can create a panoramic photoacoustic imaging by stitching many photoacoustic images together.

Another aspect of the present invention relates to using the structured light system shown in FIG. 2 to generate a strain image that is independent from the distribution of input force. According to known principles, strain imaging may be generated from calculation of Young's modulus. Force and displacement are typically used to solve for Young's Modulus. However, using a structured light system, a strain image may be generated that is independent of the magnitude of applied pressure and its distribution.

Figure 11:
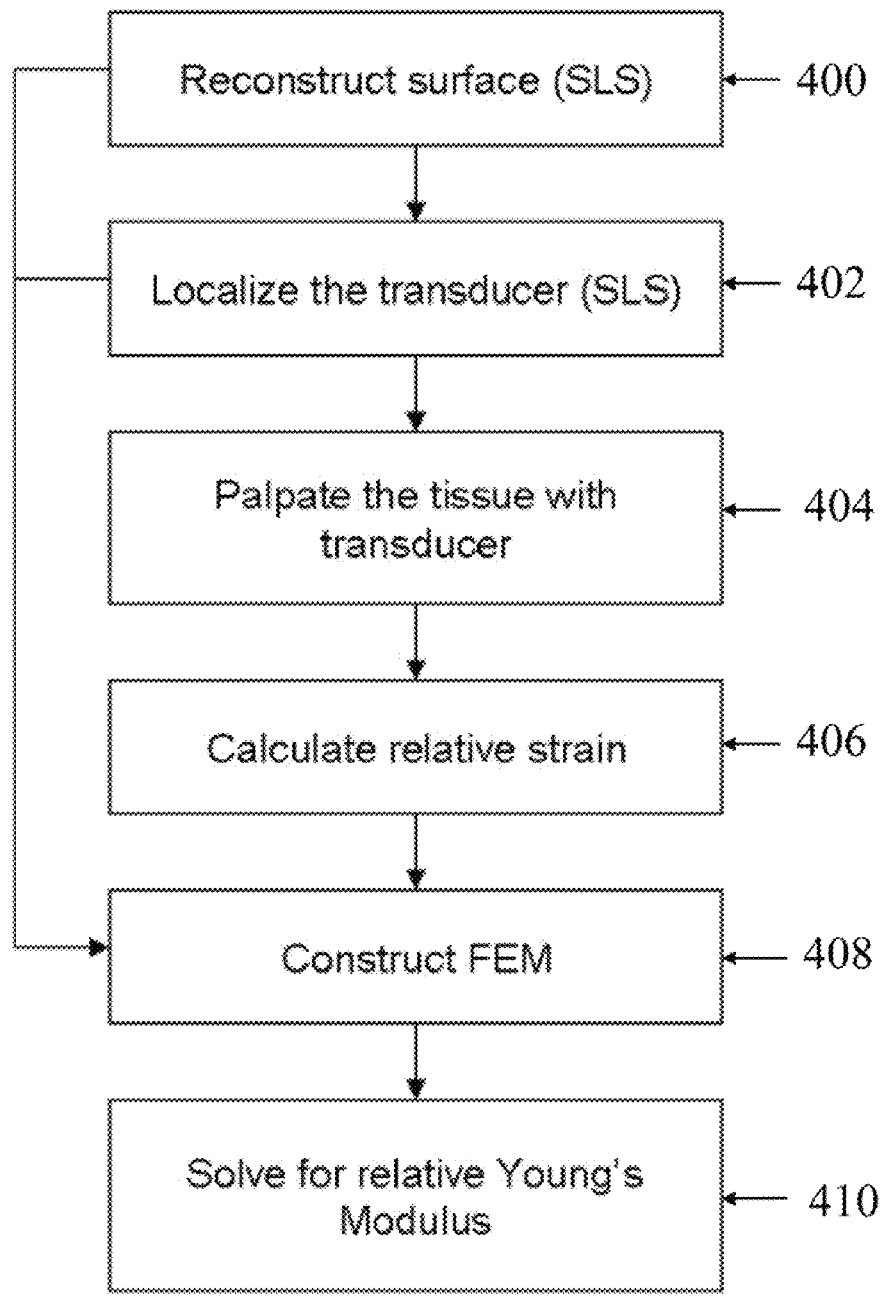
FIG. 11 is a basic flowchart of an exemplary process for calculating relative Young's Modulus according to features of the present invention.

With reference to FIG. 11, a basic flowchart of the steps for generating a strain image is described. At step 400, a structured light pattern (e.g., see FIG. 2) is projected onto a surface of a target area to be imaged. At step 400, a first set of images of the structured light pattern on the surface of the target area is acquired. The first set of images is used to reconstruct the surface of the target area, such as with a multiple channel SAD (sum of absolute differences) matching algorithm, as is known in the art. At step 402, an ultrasound probe is placed or localized onto the target area. At step 402, a second set of images is acquired which includes the surface of the target area and the ultrasound probe. The second set of images is used to determine the location of the probe with respect to the surface. That is, the structured light system tracks (and monitors) the position and orientation of the probe and tissue deformation during the palpation.

Because the shape of the probe is acquired, the position of the probe with respect to the breast may be recovered using registration techniques, such as robust ICP (iterative closest point). Alternatively, a marker may be placed on the probe for registration. However, other types of registration are possible, depending upon application and design preference.

At step 404, palpations are applied to the target area with the transducer. The strain image data is then acquired of the target area, and relative strain is calculated (step 406). At step 408, a finite element model is calculated based upon the first set of images, second set of images, and strain image data. The finite element model is then used to solve for Young's Modulus to generate a strain image (step 410).

According to the features of the present invention, the surface reconstruction given by the structured light system is assigned as the boundary condition. By incorporating the surface information from the stereo system, it is possible to initialize and solve a 3D finite element model (FEM) of the tissue and recover relative "Young's Modulus" in the area that is being imaged. The relative Young's Modulus values can be used as images themselves, and represent the true mechanical properties of the tissue, independent of the magnitude of the applied pressure and its distribution.

In addition, a structured light system may be used to aid in calibrating the ultrasound probe. An example of spatially calibrating an ultrasound probe is found in U.S. Pat. No. 7,867,167, the entire contents of which are incorporated by reference herein. As described therein, spatial calibration X is effected by solving the equation AX=XB, where A is the change in position and orientation of the probe and B is the estimated changes in position and orientation of the image. The structured light system is used to recover the transformation of the probe body from one position to another, and thus solving the equation AX=XB, as described U.S. Pat. No. 7,867,167, thus allowing for intra-operative calibration of the ultrasonic probe.

For example, a structured light pattern is projected onto a surface of the ultrasonic probe to generate a surface model of an ultrasonic probe. The surface model of the ultrasonic probe is calibrated to the ultrasound image pre-operatively. A sensor is attached to the surface of the ultrasonic probe at a sensor location. This can occur during surgery, or prior to surgery. A transformation is then determined between the surface model of the ultrasonic probe and the sensor at the sensor location. The probe calibration matrix X is computed based upon the pre-operative calibration of the surface model of the ultrasonic probe to the ultrasound image B and the transformation between the surface model of the probe and the sensor A. The equation AX=XB is then solved to determine the probe calibration matrix X. According to features of the present method, rapid calibration is obtained during the intervention which can detect any faulty condition due to EM interference, rigid-body dislocation and the like.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter. The following Example is offered by way of illustration and not by way of limitation.

Ultrasound data was acquired using a SONOLINE Antares™ ultrasound system (Siemens Medical Solutions USA, Inc.) with a high-frequency ultrasound transducer (VF10-5) at center frequency of 6-8 MHz. RF data was accessed through the Axius Direct™ Ultrasound Research Interface provided by Siemens. A data acquisition program was connected to this interface to send the command for capturing RF data. At the same time, the program collected tracking information from either a "Polaris" optical tracker (Northern Digital Inc., Waterloo, Canada) with passive markers or the "medSAFE" EM tracker (Ascension Tech. Corp.).

RF data and tracking information was captured from a breast phantom containing a harder lesion (CIRS elastography phantom, Norfolk, Va.) and ex-vivo pig liver. Alginate was injected to the liver to mark a part of liver, and then, that area was ablated. The users were asked to palpate the tissue over the hard lesion in the breast phantom and the ablated lesion in the pig liver while data was being collected. About 100 to 138 RF frames were acquired with the rate of about 30 frames per second.

Figure 5:
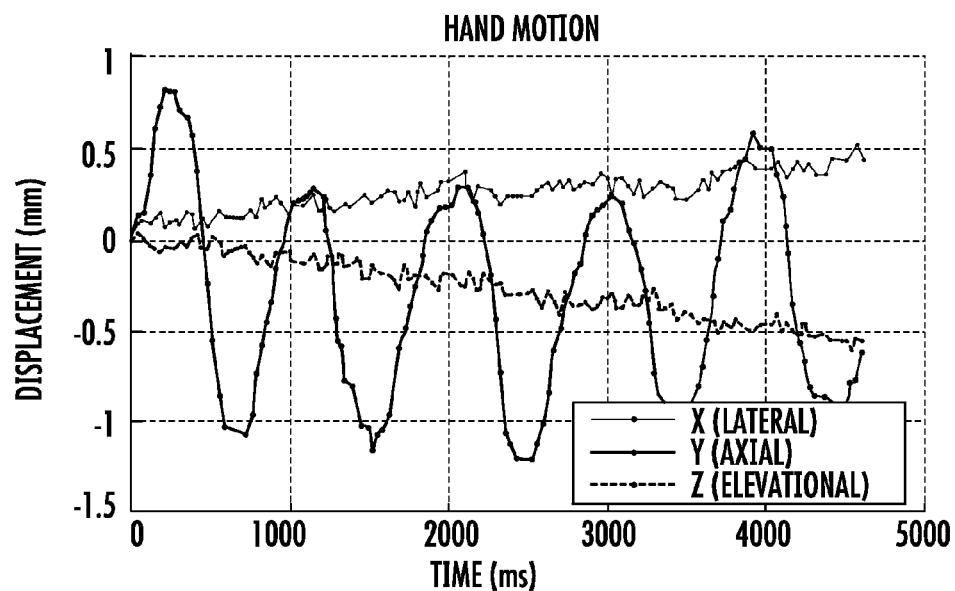
FIG. 5 is a graphical representation of the hand motion of an experienced user.

A set of data was captured by an experienced user from the breast phantom. FIG. 5 shows the translation components of hand motion as a function of time. The axial motion is dominant and there is only a gradual drift in the lateral and elevational directions. Applying compression (similar to the one shown in FIG. 5) is difficult for novice or even intermediate users. This is especially the case where axial compression does not translate into a simple up and down motion. Ultrasound gel creates a slippery surface that makes the palpation prone to out-of-plane motion. Accordingly, the present method and system aids the inexperienced user to produce high quality strain imaging.

Figure 6:
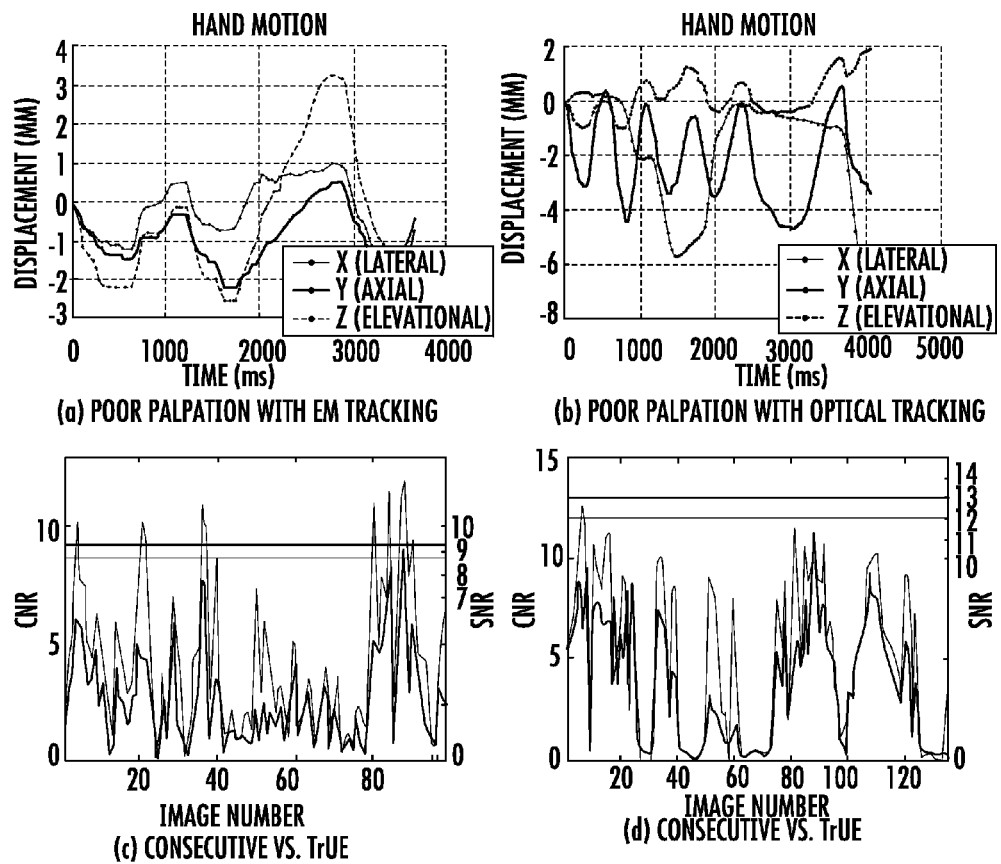
FIG. 6(a) is a graphical representation of the hand motion showing poor palpation with EM tracking.
FIG. 6(b) is a graphical representation of the hand motion showing poor palpation with optical tracking.
FIG. 6(c) is a graphical representation of the contrast-to-noise ratio (CNR) and signal-to-noise ratio (SNR) of the strain image for consecutive frames of the EM tracking versus the frames selected according to the features of the present invention.
FIG. 6(d) is a graphical representation of the contrast-to-noise ratio (CNR) and signal-to-noise ratio (SNR) of the strain image for consecutive frames of the EM tracking versus the frames selected according to the features of the present invention.

FIGS. 6(a) and 6(b) are graphical representations of the hand motions using an EM tracker and an optical tracker, respectively. In FIG. 6(a), the hand motion contains a large amount of out-of-plane motion, whereas, in FIG. 6(b), the user has moved the probe laterally. In both cases, the method and system of the present invention generate reliable results. FIGS. 6(c) and (d) show the contrast-to-noise ratio (CNR) and signal-to-noise ratio (SNR) of the strain image. The CNR and SNR value are computed from:

$$CNR = \sqrt{\frac{2(\bar{s}_b - \bar{s}_t)^2}{\sigma_b^2 + \sigma_t^2}}, SNR = \frac{\bar{s}}{\sigma}, \quad (7)$$

where s and σ denote the mean and standard deviation of intensities. The t or b subscripts show that the computation is only for the target or the background region, respectively. The SNR and CNR for computing the strain from consecutive frames (the dashed curve) is compared to the SNR and CNR of the strain image from the proposed method (solid line). Using consecutive frames is the standard method of strain imaging in ultrasound machines. Almost in all cases the method and system of the present invention outperforms the consecutive frames by a large margin.

Figure 7:
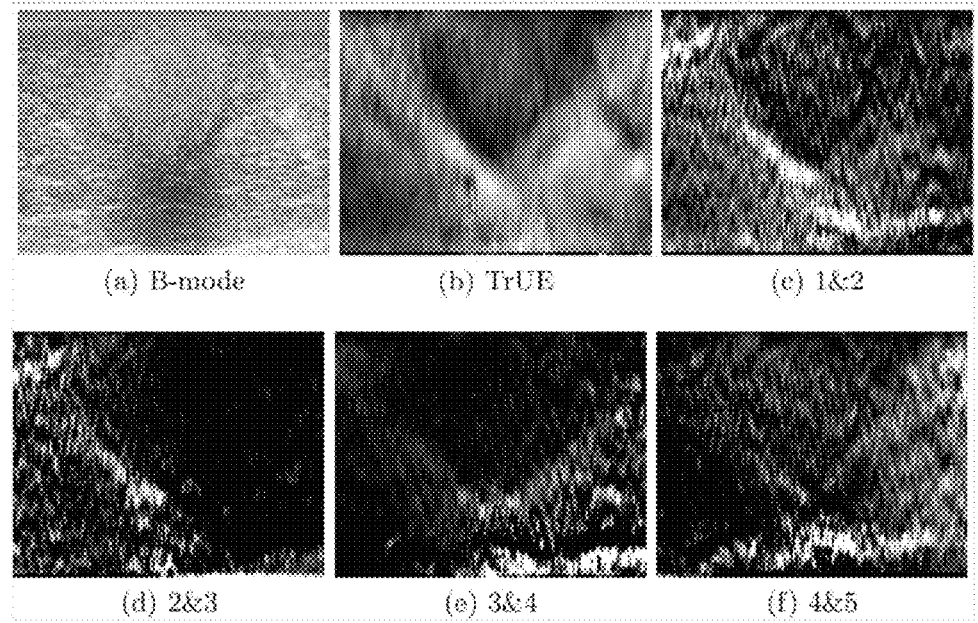
FIG. 7(a) shows a typical B-mode image generated during ultrasound imaging.
FIG. 7(b) shows the strain image formed according to features of the present invention.
FIG. 7(c) shows the strain image formed with consecutive frames 1 & 2.
FIG. 7(d) shows the strain image formed with consecutive frames 2 & 3.
FIG. 7(e) shows the strain image formed with consecutive frames 3 & 4.
FIG. 7(f) shows the strain image formed with consecutive frames 4 & 5.

Although the SNR and CNR provide quantitative measures to compare the strain images, the values do not directly reflect the visual quality of strain. In FIGS. 7(a)-(f), results are shown of strain imaging using the frame selection technique of the present invention, as well as four other strain images calculated from consecutive frames. FIG. 7(a) shows the B-mode image, FIG. 7(b) demonstrates the strain image formed according to features of the present invention, FIGS. 7(c)-(f) show strain images formed from various consecutive frames. Although improper hand motion results in poor imaging for consecutive frames, the present system and method provides a single reliable strain image. The test results show that even when the transducer had severe lateral or out-of-plane motions, the algorithm still managed to produce good results. The multi-stage frame selection and careful image fusion makes the method and system of the present invention less sensitive to tracker accuracy and robust to strain estimation failures.

The present invention exploits the information from an external tracker to create a robust framework for freehand palpation. Image pairs are selected such that in each pair, the lateral and out-of-plane motions are minimized. At the same time, the axial motion is optimized for the desired strain. Tracking data also enables fusing of multiple strain images taken roughly from the same location. The method and system can be adopted for various trackers and strain estimation algorithms, as well as different imaging modalities. In addition, the relative Young's Modulus may be calculated, which provides a more reliable image that is independent of input force distributions.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What we claim is:

1. A system for providing ultrasonic strain imaging, comprising:
    an ultrasound probe for acquiring a sequence of RF frames during palpations of a target area;
    a structured light system including a projector configured to project a structured light pattern and at least two cameras configured to acquire images;
    a processor having a non-transitory computer readable medium encoded with a program configuring the processor to:
    control the projector to project a structured light pattern onto a surface of the target area,
    control the at least two cameras to acquire a first set of images of the structured light pattern on the surface of the target area,
    control the at least two cameras to acquire a second set of images of the structured light pattern on the surface of the target area and the ultrasound probe located in the target area,
    reconstruct the surface of the target area using the first set of images,
    determine a position and orientation of the ultrasound probe within the target area based on the second set of images,
    during the palpations of the target area at each said RF frame in said sequence of RF frames, track and monitor positions and orientations of the ultrasound probe and tissue deformation based on the determined position and orientation of the ultrasound probe and the reconstructed surface of the target area respectively,
    synchronize each of said monitored positions and orientations of the ultrasound probe or the target area to a respective RF frame in said sequence of RF frames,
    compute an energy value for each RF frame with respect to all other RF frames in said sequence of RF frames using an energy function, wherein the energy function uses said monitored positions and orientations from said sequence of RF frames,
    remove RF frames beneath a threshold energy value from said sequence of RF frames;
    automatically select multiple pairs of RF frames from said sequence of RF frames by minimizing a cost function which evaluates relative motion of any two image frames based upon the monitored positions and orientations,
    calculate strain values for each of said selected multiple pairs of RF frames,
    construct a finite element model based upon the first set of images, second set of images, and strain values, and
    generate a final strain image using the finite element model to solve for Young's Modulus; and
    a display for displaying the final strain image.

2. The system of claim 1, further comprising a buffer for collecting the synchronized RF frames.

3. The system of claim 1, further comprising an external tracking device, wherein the external tracking device is an electromagnetic tracker.

4. The system of claim 1, further comprising an external tracking device, wherein the external tracking device is an optical tracker.

5. The system of claim 1, wherein the projector is configured to project a fiducial on the surface of the target area.

6. The system of claim 1, further including a CT scanner for acquiring CT scans of the target area.

7. The system of claim 1, further comprising an ablation needle configured to apply palpations towards an organ, wherein said processor is further configured to:
  track and monitor a relative position of said ablation needle for each said RF frame in said sequence of RF frames using the structured light system or an external tracking device, and
  generate said final strain image by further using the tracked and monitored relative position of the ablation needle.

8. The system of claim 1, further comprising a robotic arm configured to automatically adjust the palpations of the target area based on the tracked and monitored positions and orientations of the ultrasound probe and tissue deformation.

9. The system for providing ultrasonic strain imaging of claim 1, wherein the processor is further configured to control an indicator to provide visual hand motion feedback.

10. The system for providing ultrasonic strain imaging of claim 1, wherein the energy function is defined as $E(D_x, D_z)$, where $D_x$ and $D_z$ represent displacement in out-of-plane and lateral directions, and the energy function does not depend on axial motion.

11. The system for providing ultrasonic strain imaging of claim 1, further comprising motorized hardware incorporated into the probe and configured to provide automatic palpations of the target area based on the tracked and monitored positions and orientations of the ultrasound probe and tissue deformation.

12. A non-transitory computer-readable medium comprising software, wherein, when executed by a computer, causes the computer to:
  control a projector of a structured light system to project a structured light pattern onto a surface of a target area;
  control at least two cameras of the structured light system to acquire a first set of images of the structured light pattern on the surface of the target area;
  reconstruct the surface of the target area using the first set of images;
  control at least two cameras of the structured light system to acquire a second set of images of the structured light pattern on the surface of the target area and an ultrasound probe located in the target area;
  receive a sequence of RF frames during palpations of the target area, wherein the sequence of RF frames are received from the ultrasound probe;
  track and monitor positions and orientations of the ultrasound probe and tissue deformation during palpations of the target area at each said RF frame in said sequence of said RF frames;
  synchronize each of the positions and orientations of the ultrasound probe or the target area to a respective RF frame in the sequence of RF frames;
  compute an energy value for each RF frame with respect to all other RF frames in said sequence of RF frames using an energy function, wherein the energy function uses said positions and orientations from said sequence of RF frames,
  remove RF frames beneath a threshold energy value from said sequence of RF frames;
  select multiple pairs of RF frames from an approximately same location and orientation from said sequence of RF frames by minimizing a cost function, said cost function evaluating a relative motion of any two image frames based upon measured positions and orientations of said two image frames;
  calculate strain values for each of said selected multiple pairs of RF frames;
  calculate a finite element model based upon the first set of images, second set of images, and strain values; and
  generate a final strain image using the finite element model to solve for Young's Modulus.

* * * * *